United States Patent
Kim et al.

(10) Patent No.: US 10,123,558 B2
(45) Date of Patent: Nov. 13, 2018

(54) LEUCONOSTOC CITREUM AND FERMENTED FOODS USING THE SAME AS A STARTER, AND COMPOSITIONS THEREOF

(71) Applicant: CJ CHEILJEDANG CORP., Seoul (KR)

(72) Inventors: Bong Joon Kim, Incheon (KR); Ji-Young Oh, Seongnam-si (KR); Min-Soo Kwon, Yongin-si (KR); Heon Woong Jung, Seoul (KR); Kang-Pyo Lee, Seoul (KR)

(73) Assignee: CJ CHEILJEDANG CORP., Seoul (KR)

( * ) Notice: Subject to any disclaimer, the term of this patent is extended or adjusted under 35 U.S.C. 154(b) by 30 days.

(21) Appl. No.: 15/276,069

(22) Filed: Sep. 26, 2016

(65) Prior Publication Data
US 2017/0006905 A1    Jan. 12, 2017

Related U.S. Application Data

(63) Continuation of application No. 13/380,152, filed as application No. PCT/KR2009/005139 on Sep. 10, 2009.

(30) Foreign Application Priority Data

Jul. 16, 2009  (KR) .................. 10-2009-0065024
Aug. 19, 2009  (JP) .................. 2009-190443

(51) Int. Cl.
*A23L 19/20* (2016.01)
*A23L 29/00* (2016.01)
(Continued)

(52) U.S. Cl.
CPC .............. *A23L 19/20* (2016.08); *A23K 10/18* (2016.05); *A23L 29/065* (2016.08);
(Continued)

(58) Field of Classification Search
CPC ........................................................ A23L 1/23
(Continued)

(56) References Cited

U.S. PATENT DOCUMENTS

2006/0029692 A1 * 2/2006 Kang ...................... A23L 11/07
426/52
2007/0009503 A1   1/2007 Uehara et al.

FOREIGN PATENT DOCUMENTS

| KR | 100736835 B1 | 7/2007 |
| KR | 100814665 B1 | 3/2008 |
| KR | 101099924 B1 | 12/2011 |

OTHER PUBLICATIONS

Choi et al., "Novel Leuconostoc citreum starter culture system for the fermentation of Kimchi, a fermented cabbage product", Antoine van Leeuwenhoek, 2003, vol. 84, pp. 247-253.
(Continued)

*Primary Examiner* — D. Lawrence Tarazano
*Assistant Examiner* — Philip A Dubois
(74) *Attorney, Agent, or Firm* — Birch, Stewart, Kolasch & Birch, LLP

(57) ABSTRACT

The present invention relates to *Leuconostoc citreum* CJGN34 KCTC 10974BP lactic acid bacteria, fermented foods including kimchi manufactured using the lactic acid bacteria as a starter, and lactic acid bacteria composition comprising of the lactic acid bacteria. The novel *Leuconostoc citreum* CJGN34 of the present invention enhances the general taste quality of kimchi; increases the intrinsic complex sour taste and carbonated taste of kimchi manufactured by traditional manufacturing method in wintertime; and
(Continued)

regularly sustains the fermentation quality during the year; particularly, has an effect for controlling the deterioration of fermentation quality in the summer in which the taste quality deteriorates. Thus, the lactic acid bacteria of the present invention can be used as a starter in fermented foods including kimchi, or as a drug medicine in the form of a tablet or capsule mixed with carriers or additives, or a s probiotics for foods; or applied in cosmetic ingredients by mixing in a certain amount. Therefore, the lactic acid bacteria of the present invention can be used in a manner commonly applied in various fields of technology such as medicine, food, feed, cosmetics or the like.

12 Claims, 1 Drawing Sheet

(51) Int. Cl.
    *A61K 8/99*       (2017.01)
    *C12N 1/20*       (2006.01)
    *C12R 1/01*       (2006.01)
    *A61Q 19/00*     (2006.01)
    *A23L 33/135*    (2016.01)
    *A23K 10/18*     (2016.01)

(52) U.S. Cl.
    CPC .............. *A23L 33/135* (2016.08); *A61K 8/99* (2013.01); *A61Q 19/00* (2013.01); *C12N 1/20* (2013.01); *C12R 1/01* (2013.01); *A23V 2002/00* (2013.01); *A23Y 2260/21* (2013.01); *A61K 2800/10* (2013.01)

(58) Field of Classification Search
    USPC .......................................................... 426/61
    See application file for complete search history.

(56) References Cited

OTHER PUBLICATIONS

Kim et al., "Complete Genome Sequence of Leuconostoc citreum KM20", J. Bacteriology, 2008, vol. 190, pp. 3093-3094.

Kim et al., "*Leuconostoc inhae* sp. nov., A Lactic Acid Bacterium Isolated From Kimchi", Int'l J. of Systemic and Evolutionary Microbiology, 2003, vol. 53, pp. 1123-1126.

\* cited by examiner

LEUCONOSTOC CITREUM AND FERMENTED FOODS USING THE SAME AS A STARTER, AND COMPOSITIONS THEREOF

CROSS REFERENCE TO RELATED APPLICATIONS

This application is a Continuation of copending application Ser. No. 13/380,152, filed on Dec. 22, 2011, which was filed as PCT International Application No. PCT/KR2009/005139 on Sep. 10, 2009, which claims the benefit under 35 U.S.C. § 119(a) to Patent Application No. 2009-190443, filed in Japan on Aug. 19, 2009, and Patent Application No. 10-2009-0065024, filed in the Republic of Korea on Jul. 16, 2009, all of which are hereby expressly incorporated by reference into the present application.

FIELD OF THE INVENTION

The present invention relates to *Leuconostoc citreum* bacteria, fermented foods using the bacteria as a starter, and compositions containing the bacteria. More particularly, the present invention relates to *Leuconostoc citreum* which can induce fermentation flavor and taste quality of Kimchi manufactured in winter throughout a year and, more importantly, can effectively inhibit deterioration of fermentation quality in summer, fermented foods using the bacteria as a starter, and compositions containing the bacteria.

BACKGROUND OF THE INVENTION

Kimchi is a collective name of fermented vegetable foods representing Korea, which are prepared by salting various vegetables, blending with various seasonings and naturally aging. Especially, representative Kimchi is Gimjang (김장) Kimchi, a main ingredient of which is Korean cabbage, i.e., *Brassica campestris L*. Gimjang Kimchi is prepared by salting Korean cabbage and radish harvested at late autumn to early winter, blending them with sub-ingredients such as garlic, ginger, green onion and so on and burying them underground and is served as winter food (Cheigh and Park, Biochemical, microbiological and nutritional aspects of Kimchi, *Crit. Rev. FoodSci. Nutr.* Vol. 34, 1981, pages 102-127). Like this, Gimjang Kimchi is categorized as cold fermentation preserves and is manufactured by keeping vegetables at low temperature during winter season when vegetables are not produced, through salting and fermentation methods. Gimjang Kimchi is served as sources of carbon, amino acid and vitamins and provides a rich fermentation flavor formed from processes of fermentation and aging with unique lactic acid bacteria in raw materials.

Recently, however, raw materials such as Korean cabbages can be produced and stored throughout a year owing to bread improvement and cultivation development and, therefore, Korean cabbage Kimchi can be manufactured even though it is not Gimjang season (i.e., winter). Further, the spread of refrigerator and Kimchi refrigerator have enables cold fermentation preservation as if it were winter. As a result, recent Kimchi is no more the same with the traditional Korean cabbage Gimjang Kimchi.

Basically, the quality of Kimchi significantly changes depending on that of various raw materials such as Korean cabbage which is recently forwarded throughout a year. The quality change of Kimchi has become an obstacle to providing products having constant quality with customers, especially in a position of business companies commercializing Kimchi. Especially, Kimchi manufactured in summer (June~August) has problems like low quality of raw materials and deterioration of fermentation-aging flavor even though the Kimchi would be manufactured by the same fermentation and aging methods as in winter. It is well known in the art that a wide variation in quality depending on season has brought about various claims of quality dissatisfaction by customers.

Prior arts for solving the problems have tried to control Kimchi quality by adding various microorganisms, mainly lactic acid bacteria, as a starter (Korean Patent Nos. 10-0536108, 10-0181009, 10-0330674 and so on). The prior arts, however, applied starters merely for improving quality or confirmed that there is a difference of general taste quality in sensory test, regardless of season; they did not investigate causes of quality change during a year. Accordingly, there is no prior art that focuses on the quality improvement of summer Kimchi, analyzes the causes of quality deterioration and solves the problems.

Meanwhile, Kimchi lactic acid bacteria such as *Leuconostoc Kimchii, Leuconostoc citreum, Leuconostoc mensenteroides, Leuconostoc gasicomitatum, Leuconostoc lactis, Lactobacillus plantarum* and *Lactobacillus sakei* have been used individually or in combination in manufacturing various fermented foods.

Among them, *Leuconostoc citreum* bacteria is concerned in Kimchi aging and is known as its ability to produce polymer mucilages, dextran, with sugar (Korean Patent No. 10-0718344) and as being effective for treatment and prevention of atopic dermatitis (Korean Patent Application No. 10-2005-0041572). Further, Korean Patent No. 10-0814665 discloses *Leuconostoc citreum* S5 bacteria producing dextran and a method of producing fermented products comprising the dextran by using the bacteria and Korean Patent No. 10-080053 discloses *Leuconostoc citreum* producing mannitol and a method of producing mannitol using the bacteria.

SUMMARY OF THE INVENTION

The present inventors analyzed fermentation patterns of Korean cabbage Kimchi during a year and monitored the changes of lactic acid bacteria flora and organic acids which cause changes of fermentation quality.

By doing so, the present inventors found out that lactic acid bacteria isolated from Kimchi manufactured in winter when the most delicious Kimchi can be manufactured, have a significant role in improving and stabilizing quality throughout a year. Further, the present inventors found out that the lactic acid bacteria can induce the fermentation flavor and taste quality of winter Kimchi and effectively inhibit deterioration of fermentation quality in summer.

Therefore, a purpose of the present invention is to provide a novel *Leuconostoc* spp. lactic acid bacteria which can be used as a starter for Kimchi, induce fermentation flavor and taste quality of winter Kimchi and effectively inhibit deterioration of fermentation quality in summer.

Further, another purpose of the present invention is to provide fermented foods manufactured by using the novel *Leuconostoc* spp. lactic acid bacteria as a starter.

In addition, another purpose of the present invention is to provide a bacteria composition containing the novel *Leuconostoc* spp. lactic acid bacteria.

In order to achieve such purposes, the present invention provides *Leuconostoc citreum* CJGN 34 (*Leuoostoc cit-* reum CJGN34) (Deposited with Korean Type of Collection Culture (KCTC) on 2006. 07. 27, Accession number: KCTC 10974BP).

Further, the present invention provides a starter composition for fermenting foods, which contains *Leuconostoc citreum* CJGN 34 as an active ingredient.

In addition, the present invention provides fermented foods such as Kimchi manufactured by using the starter compositions.

In addition, the present invention provides a lactic acid bacteria composition containing *Leuconostoc citreum* CJGN 34 as an active ingredients.

A term 'active ingredient' used in this specification means a material or materials group (including medicinal herbs containing any unidentified pharmaceutical active ingredient) which is contained as a main component and is expected to exhibit directly or indirectly pharmaceutical efficacy or effect of a medicament via inherent pharmacological action.

DETAILED DESCRIPTION OF THE INVENTION

Figure 1:
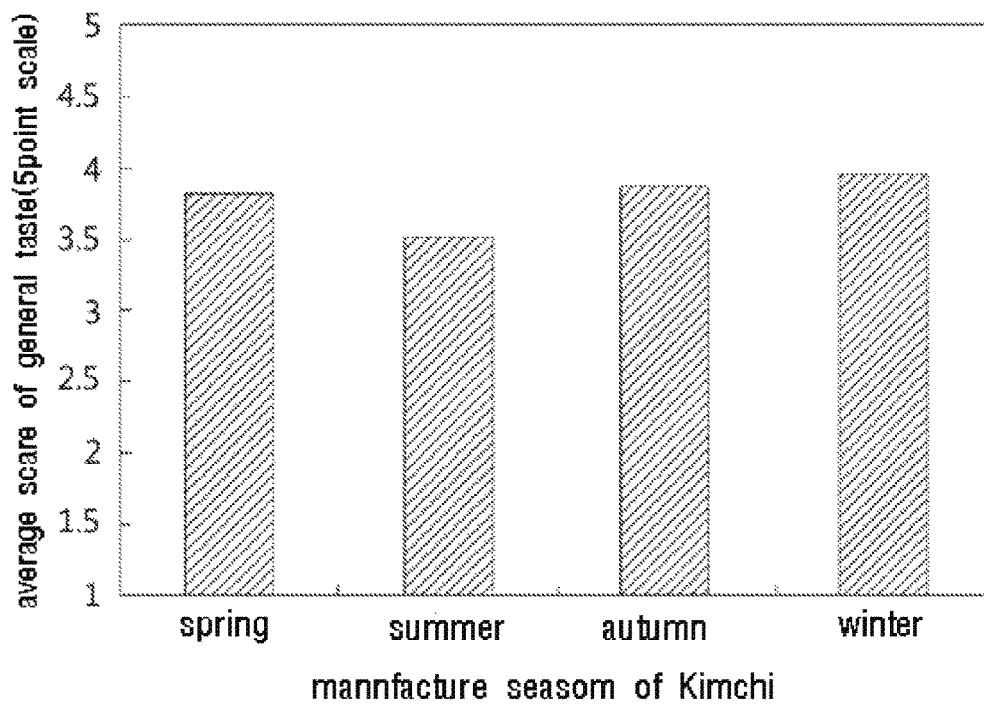
FIG. 1 is a graph showing the mean of general taste scores depending on season when Kimchi was made.

The present invention is more particularly explained as follows.

*Leuconostoc citreum* CJGN 34 of the present invention is characterized by being a novel *Leuconostoc citreum* bacteria isolated from Kimchi and identified. Although the bacteria was isolated from Kimchi manufactured at Gimjang season (i.e., winter), it does not mean that a range of the bacteria according to the present invention is limited thereto.

According to analysis results of 16S rRNA base sequence for identifying and classifying a microorganism, *Leuconostoc citreum* CJGN 34 of the present invention has the highest homology with *Leuconostoc citreum* reference bacteria (*Leuconostoc citreum* KCTC $3256^T$, GenBank accession number AF11948), which means that the *Leuconostoc citreum* CJGN 34 of the present invention has the closest molecular phylogenetic relationship with *Leuconostoc citreum*. Therefore, the microorganism was identified as *Leuconostoc citreum*, named as *Leuconostoc citreum* CJGN34 and deposited to Korea Research Institute of Bioscience and Biotechnology (KRIBB) on Jul. 27, 2006 (Accession number: KCTC 10974BP).

*Leuconostoc citreum* CJGN 34 of the present invention is gram positive bacteria and facultative anaerobe which can grow under an aerobic or anaerobic condition. Further, *Leuconostoc citreum* CJGN 34 of the present invention does not form an endospore, has no motility and has a shape of monococcus or diplococcus. Conventional methods in the art were performed to analyze the specific shape and physiological properties of *Leuconostoc citreum* CJGN 34 and the result is summarized as following table 1.

TABLE 1

| | |
|---|---|
| mannitol | + |
| sorbitol | − |
| D-mannoside | − |
| D-glucoside | + |

TABLE 1-continued

| | |
|---|---|
| glucosamine | + |
| amygdaline | + |
| arbutin | + |
| esculine | + |
| salicin | + |
| cellobiose | + |
| maltose | + |
| lactose | − |
| melibiose | − |
| saccharose | + |
| trehalose | + |
| inulin | − |
| melizitose | − |
| D-raffinose | − |
| amidon | − |
| glycogen | − |
| xylitol | − |
| gentiobiose | − |
| D-turanose | + |
| D-lyxose | − |
| D-tagatose | − |
| D-fucose | − |
| D-arabitol | − |
| L-arabitol | − |
| gluconate | − |
| 2-gluconate | − |
| 5-gluconate | − |

+: positive
−: negative

Preferably, *Leuconostoc citreum* CJGN 34 of the present invention may be stored at −70° C. after being added into a preservation liquid made of water and glycerol in an amount or be lyophilized after being suspended in sterilized 10% skim milk, for a prolonged stable storage.

Further, *Leuconostoc citreum* CJGN 34 of the present invention, which is lactic acid bacteria isolated from naturally-fermented Kimchi, was classified as GRAS (Generally recognized as safe) bacteria for a human being and confirmed as being negative in all of the safety assessment such as gelatin liquefaction test, phenylalanine deaminase test, ammonification test and hemolysis test, which means that the bacteria is safe as food materials.

In case that *Leuconostoc citreum* CJGN 34 according to the present invention is used in fermented foods such as Kimchi as a starter, it may improve the general taste quality of the foods, maintain the fermentation quality constantly throughout a year by improving a complex sour and carbonated taste which is a representative taste of Gimjang Kimchi traditionally manufactured in winter and, especially, effectively inhibit deterioration of fermentation quality in summer when taste quality is declined.

Further, a bacteria composition may be made by culturing and harvesting bacterial flora including the bacteria. The bacteria composition may be used according to conventional methods in various industries such as feed probiotics after being blended with feed materials such as grain powder; food probiotics or medicaments probiotics in a form of tablets or capsules after being blended with carriers or additives; or cosmetics after being blended with the other cosmetic ingredients in an amount.

Further, *Leuconostoc citreum* CJGN 34 according to the present invention may be used in a lactic acid bacteria pharmaceutical composition. In this case, it may be formulated into conventional pharmaceutical dosage forms known to the art. It may be preferably formulated into oral dosage forms such as liquid, suspension, powder, granule, tablet, capsule, bolus, pellet or extract.

In formulating into a respective dosage form, pharmaceutically acceptable and required carriers or additives may be added in manufacturing the dosage form. For example, at least one carrier selected from diluents, slip agents, binding agents, disintegrating agents, sweetening agents, stabilizers and preservative agents; and at least one additive selected from flavoring agents, vitamins and antioxidants may be used in formulating the oral dosage forms.

Any pharmaceutically acceptable carriers and additives may be used. Specifically, it may be preferable that lactose, corn starch, soybean oil, microcrystalline cellulose or mannitol is used as diluents; magnesium stearate or talc is used as slip agents; polyvinylpyrrolidone or hydroxypropylcellulose is used as binding agents. Further, it may be preferable that carboxymethylcellulose calcium, sodium starch glycolate, polacrilin potassium or crospovidone is used as disintegrating agents; white sugar, fructose, sorbitol or aspartame is used as sweeting agents; sodium carboxymethylcellulose, β-cyclodextrin, white wax or xanthan gum is used as stabilizers; and methyl p-hydroxybenzoate, propyl p-hydroxybenzoate or potassium solvate is used as preservative agents.

Further, in addition to the above ingredients, natural herbs with Mae-sil (japanese apricot) flavor, lemon flavor, pineapple flavor or herb flavor, natural fruit juice, natural pigments such as chlorophyllin or flavonoid, sweeting ingredients such as fructose, honey, sugar alcohol or sugar, acidifiers such as citric acid or sodium citrate may be used after mixing for a purpose of raising appetite.

Formulating methods and carriers and additives necessary for such formulating are detailed in Remington's Pharmaceutical Sciences (19th ed., 1995).

Further, *Leuconostoc citreum* CJGN 34 according to the present invention may be used in a lactic acid bacteria food composition. The food composition covers conventional daily-consumed general foods as well as health foods. If the food composition is used in the health foods, it may be formulated into conventional health food dosage forms known to the art, with sitologically acceptable carriers or additives. The health foods may be formulated, for example, into powder, granule, tablet, capsule, suspension, emulsion, syrup, liquid, extract, jelly or drink form. As sitologically acceptable carriers or additives, an arbitrary carrier or additive usable in any forms to prepare may be used.

Further, since *Leuconostoc citreum* CJGN 34 according to the present invention may comprise dextran, a polymer with high absorbability of moisture, it can be used in a lactic acid bacteria cosmetic composition. The cosmetic composition according to the present invention may be formulated into conventional form known to the cosmetic industries. Any carrier or additive which is acceptable and necessary in manufacturing a specific cosmetic form may be added.

Further, *Leuconostoc citreum* CJGN 34 according to the present invention may be used in lactic acid bacteria feed additives or feed compositions.

Used in the feed additives, the composition may be manufactured into a form of 20 to 90% highly concentrated liquid, powders or granules. The feed additive may additionally include at least one selected from organic acids such as citric acid, humalic acid, adipic acid, lactic acid and malic acid; phosphates such as sodium phosphate, potassium phosphate, acidic pyrophosphates and polyphosphates (condensed phosphate); and natural antioxidants such as polyphenols, catechins, alpha-tocopherols, rosemary extracts, vitamin C, green tea extracts, licorice extracts, chitosan, tannic acids and phytic acids. Used in the feed composition, the composition may be manufactured into a conventional animal feed form and include conventional feed ingredients.

The feed additives and the animal feed may additionally include crops, for example, crushed or shredded wheat, oats, barley, corn and rice; vegetable protein feeds, for example, feeds mainly consisting of rape, soybean and sunflower; animal protein feeds, for example, blood meal, meat meal, bone meal and fish meal; and sugar and dairy products, for example, various dry ingredients consisting of milk powder and whey powder, and may further include nutritional supplements, digestion- and absorption-enhancers and growth promoters.

The feed additives may be administered to animals individually or in combination with other additives selected from edible carriers. Further, the feed additives may be topdressing, may be directly mixed with animal feeds or may be easily administered to animals as oral dosage forms separately from animal feeds. In case of being administered separately from animal feeds, the feed additives may be combined with pharmaceutically acceptable edible carriers and prepared into immediate-release formulations or sustained-release formulations, as well known in the art. The edible carriers may be solid or liquid, for example, corn starch, lactose, sucrose, soy flake, peanut oil, olive oil, sesame oil and propylene glycol. In case solid carriers are used, the feed additives may be in a form of tablet, capsule, powder, troche or lozenge, or may be a not-dispersed topdressing. If liquid carriers are used, the feed additives may have a form of soft gelatin capsules, syrup, suspension, emulsion or solution.

The feeds may include an arbitrary protein-containing organic grain flour which has been conventionally used to meet animals' appetite. The protein-containing grain flour typically consists of corn or soybean flour or is a mix of corn/soybean flour.

In addition, the feed additives and the animal feeds may contain adjuvants such as preservatives, stabilizers, wetting agents, emulsifiers and liquefying agent. The feed additives may be added to animal feeds by means of dipping, spraying or mixing for use.

The animal feeds or feed additives according to the present invention may be applied to a diet for various animals such as mammals, poultry and fish. The mammals may be pets (for example, dogs, cats) as well as pigs, cows, sheep, goats and laboratory rodents; poultry such as chickens, turkeys, ducks, geese, pheasant and quail; and fish such trout, without limitation thereto.

As disclosed in the above, in case of novel *Leuconostoc citreum* CJGN 34 according to the present invention being used as a starter for fermented foods such as Kimchi, it may improve general taste quality, increase a complex sour and carbonated taste which is a unique taste of Kimchi manufactured by traditional methods in winter and, consequently, maintain constant fermentation quality throughout a year and effectively inhibit deterioration of fermentation quality in summer when taste quality of Kimchi deteriorates. Novel *Leuconostoc citreum* CJGN 34 according to the present invention may be utilized as a starter for fermented foods such as Kimchi after being prepared as a bacteria composition; as food or medicament probiotics in a form of tablet or capsule after being mixed with carriers or additives; or cosmetic materials after mixing with other cosmetic materials in an amount. That is, novel *Leuconostoc citreum* CJGN 34 according to the present invention may be utilized in various industries such as medicaments, foods, feeds and cosmetics.

Hereinafter, the present invention will be described by the following examples in more detail. However, the purpose of these examples is only illustrating the present invention, not limiting the scope of the invention thereto in any way.

EXAMPLE 1

Deducting Improvement Aspects by Monitoring Kimchi Quality Change During a Year and Isolating GN34 Bacteria Quality change of Kimchi was monitored during a year in order to find the causes of quality change and to improve the quality.

Kimchi manufactured according to the manufacture method of CJ CheilJedang was used. The Kimchi manufactured between March and May, 15 was classified as spring Kimchi; that manufactured between May, 16 and August as summer Kimchi; that manufactured between September and November 15 as autumn Kimchi; and that manufactured between November 16 and February as winter Kimchi.

As a result of analyzing the taste quality of the Kimchi manufactured in each season in a sensory test by 5-point scale, it was found that the summer Kimchi has a low value of about 3.5 for a general taste item, whereas the Kimchi manufactured in the other season has an average range of 3.8 to 4.0. The above results are shown in the FIG. 1.

Figure 2:
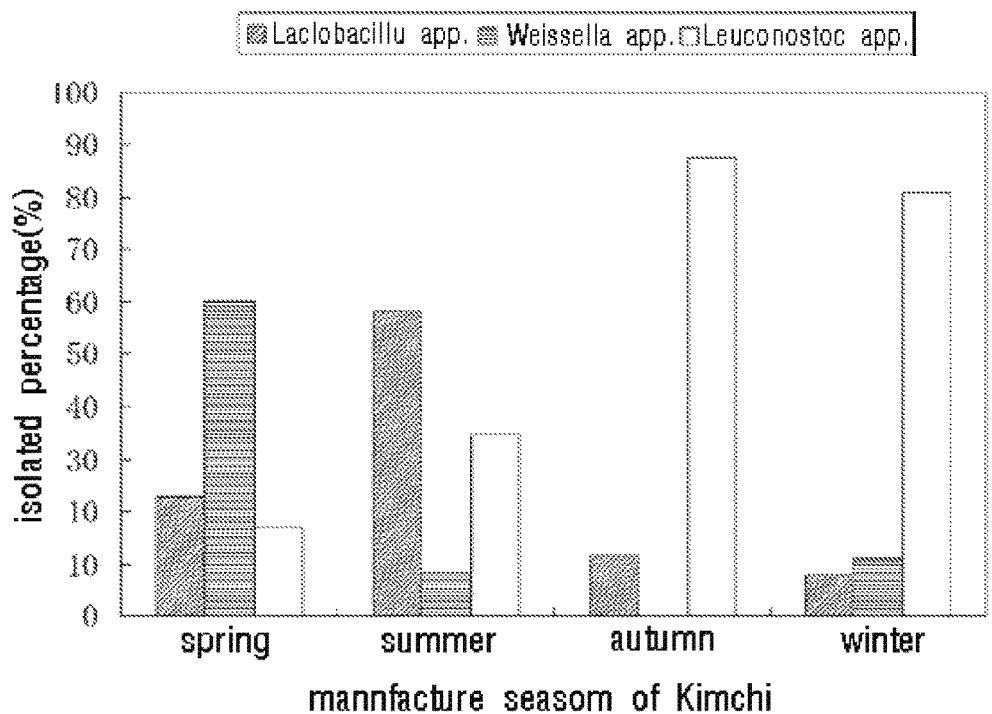
FIG. 2 is a graph showing the percentage of bacteria isolated from fermentation bacteria flora depending on season when Kimchi was made.

In order to analyze the fermenting microbial effect on change of the taste quality throughout a year, identification was performed by 16S rRNA analysis according to the method disclosed in Choi (Choi et. al, Microbial population dynamics of kimchi, a fermented cabbage, FEMS microbial. Lett., Vol. 257, 2006, pages 262-267). The result indicates that the Kimchi manufactured during traditional Gimjang season, i.e., in winter, has more than 80% *Leuconostoc* spp. producing various acid and gas, besides lactic acid, with sugar through a process of an absolute hetero fermentation. Since the Kimchi manufactured in winter has the most outstanding taste quality, it may be concluded that *Leuconostoc* spp. has an important effect in providing complex fermentation flavor and carbonated taste of winter Kimchi. On the other hand, it was found that the ratio of *Lactobacillus* spp. causing partial hetero fermentation or homo fermentation wherein only lactic acid, not gas, is produced using sugar under a general environment, for example, *Lactobacillus sakei, Lactobacillus curvatus* and *Lactobacillus plantarum* was more than 50% in the Kimchi manufactured in summer when fermentation quality is deteriorated. The ratio is higher than that of the Kimchi manufactured in the other seasons, which leads to a conclusion that the change of fermentation bacteria flora may be a cause of simple sour taste and weak carbonated taste of the summer Kimchi. The above results are shown in FIG. 2.

In order to clarify the effect of fermentation bacteria flora change on the fermentation flavor of Kimchi, an HPLC analysis of organic acids was performed on the same sample as that used in microorganism analysis, according to the methods of the Choi. In the sample, fermentation had begun and total acidity was more than 0.4%. The organic acids correspond to main metabolites which lactic acids produce after consuming sugar. Since lactic acid is mainly produced in partial hetero fermentation or homo fermentation and acetic acid and carbon dioxide as well as lactic acid are produced as fermentation products in absolute hetero fermentation, organic acids are major marker informing the kind of fermentation. The analysis results are shown in Table 2.

As known from the table 2, the molar ratio of lactic acid to acetic acid in the spring Kimchi, autumn Kimchi and winter Kimchi was in a range of about 1.3~1.6, whereas that in the summer Kimchi was in a range of about 2.2~2.8, which means the proportion of Lactic acid increased. It may conclude that the change of fermentation lactic acid bacteria increase in homo fermentation, especially in summer, which is responsible for quality deterioration of summer Kimchi.

TABLE 2

| manufacture season | sample No. | concentration ratio of Lactic acid/Acetic acid |
|---|---|---|
| spring | spring Kimchi 1 | 1.5 ± 0.08 |
| spring | spring Kimchi 2 | 1.6 ± 0.11 |
| summer | summer Kimchi 1 | 2.8 ± 0.13 |
| summer | summer Kimchi 2 | 2.2 ± 0.09 |
| summer | summer Kimchi 3 | 2.4 ± 0.25 |
| summer | summer Kimchi 4 | 2.8 ± 0.13 |
| autumn | autumn Kimchi 1 | 1.4 ± 0.09 |
| winter | winter Kimchi 1 | 1.4 ± 0.25 |
| winter | winter Kimchi 2 | 1.5 ± 0.39 |
| winter | winter Kimchi 3 | 1.3 ± 0.02 |
| winter | winter Kimchi 4 | 1.3 ± 0.09 |

Based on the above result, the present inventors could manufacture Kimchi with the constant fermentation quality throughout a year by applying lactic acid bacteria isolated from winter Kimchi having the best taste quality, as a starter. Further, the present inventors could isolate around 500 bacteria from winter Kimchi in order to inhibit deterioration of the fermentation quality of summer Kimchi. Especially, the present inventors could isolate novel lactic acid bacteria which are absolute hetero fermentation bacteria and dominant species of winter Kimchi and meet the purpose of the present invention.

EXAMPLE 2

Isolation and Identification of Microorganism *Leuconostoc citreum* CJGN34 Bacteria In the above Example 1, the causes responsible for the quality change of Kimchi during a year were analyzed and lactic acid bacteria were isolated from the well-aged delicious winter Kimchi. The lactic acid bacteria were named as *Leuconostoc citreum* CJGN34. Lactic acid bacteria *Leuconostoc citreum* CJGN34 were streaked onto solid MRS medium (Difco, USA) containing 1.5% agar and incubated at 30° C. for 24 hrs. Colonies confirmed as being purely separated were taken by a loop and incubated with MRS broth (Difco, USA) at 30° C. for 18 to 24 hrs.

Then, the morphology and physiological properties of *Leuconostoc citreum* CJGN34 bacteria were determined with API50CH and API50CHL kits (Bio-Me'reux) according to the methods disclosed in Kim et. al, *Leuconostoc inhae* sp. nov., a lactic acid bacterium isolated from kimchi, International Journal of Systematic and Evolutional Microbiology, Volume 53, July 2003, pages 1123-1126. The resultant morphology and physiological properties of *Leuconostoc citreum* CJGN34 bacteria were summarized in the above table 1.

Further, a sequence of 16S rRNA gene was analyzed for identification and classification of the lactic acid bacteria. The sequence of 16S rRNA gene was determined and analyzed according to a method disclosed in Kim et. al, *Leuconostoc kimchii* sp. nov., a new species from kimchi. International Journal of Systematic and Evolutional Microbiology, Volume 50, September 2000, pages 1915-1919.

Since *Leuconostoc citreum* CJGN34 according to the present invention has the highest homology (99.7%) with *Leuconostoc citreum* reference bacteria (KCTC 3526T, GenBank accession number AF111948), *Leuconostoc citreum* CJGN34 according to the present invention was identified as *Leuconostoc citreum*, named as *Leuconostoc citreum* CJGN34 and deposited to Korea Research Institute of Bioscience and Biotechnology(KRIBB) July 27, 2006 (Accession number: KCTC 10974BP).

EXAMPLE 3

Safety Assessment of *Leuconostoc citreurn* CJGN34

Hemolysis test, gelatin liquefaction test, hazardous metabolite (ammonification) test and phenylalanine deaminase test were performed according to the safety assessment methods suggested by the standard of Korea Biotechnology Industry Organization to assess safety of the bacteria isolated from the Example 1. The obtained result is summarized in table 3.

TABLE 3

Safety assessment for *Leuconostoc citreum* CJGN34

| bacteria | tests | | | |
|---|---|---|---|---|
| | gelatin liquefaction | phenylalanine deaminase | hemolysis | ammonification |
| CJGN34 | negative | negative | negative | negative |

Based on the above result, *Leuconostoc citreum* CJGN34 was found negative in all of the gelatin liquefaction test, hazardoug metabolite (ammonification) test, phenylalanine deaminase test and hemolysis test. Accordingly, *Leuconostoc citreum* CJGN34 was confirmed as being safe for administration to a human being.

EXAMPLE 4

Characteristics of Kimchi Manufactured by using *Leuconostoc citreum* CJGN34 as a Starter A bacteria culture or a bacteria composition was prepared as follows to apply *Leuconostoc citreum* CJGN34 according to the present invention as a starter.

Culture medium was prepared by dissolving 10 g of glucose, 5 g of yeast extracts and 5 g of diammonium citrate into water, sterilizing, inoculating with bacteria and incubating at 25~37° C. for 8 to 24 hrs. A bacteria composition was prepared as follows: bacteria were incubated and grown at 30° C. for around 18 hrs with pH adjustment of MRS broth (Difco) into 5.5~7.0 by ammonia gas and centrifuged for recovery. Recovered bacteria were lyophilized below −40° C. with a cryoprotectant consisting of dextrin 5% and skim milk 10%, dried at the temperature of 30~37° C. and ground into powder by a mixer. Powdered viable cells were counted to a desired value, mixed with a suitable amount of excipients such as glucose, lactose and skim milk and packaged in a sealable aluminium pouch.

The culture medium or the bacteria composition manufactured according to the above was added in an amount of 0.001%~3% based on the total weight of Kimchi in manufacturing Kimchi. Kimchi was fermented and aged according to the manufacturing method of CJ Cheiljedang. Further, a sensory test and physiochemical analyses were performed with two (2) kinds of Kimchi made of the same raw materials and composition ratio, one of which was fermented with a starter *Leuconostoc citreum* CJGN34 and the other of which was fermented naturally without a starter. Since the result may be different depending on aging, the aging was adjusted within a range of 0 to 0.05% based on the total acidity. The sensory test result for the Kimchi manufactured in the above is shown in table 4.

TABLE 4

| manufacture season | sample | General taste preference | Sourness preference | carbonated taste preference | Aftertaste preference |
|---|---|---|---|---|---|
| Summer | naturally fermented Kimchi | 3.59 | 3.22 | 3.49 | 3.36 |
| Summer | starter Kimchi | 3.85 | 3.67 | 3.61 | 3.81 |
| Winter | naturally fermented Kimchi | 4.01 | 3.81 | 3.71 | 3.76 |
| Winter | starter Kimchi | 4.05 | 3.92 | 3.82 | 3.79 |
| Spring | naturally fermented Kimchi | 3.81 | 3.66 | 3.68 | 3.68 |
| Spring | starter Kimchi | 3.91 | 3.71 | 3.75 | 3.72 |
| Autumn | naturally fermented Kimchi | 3.86 | 3.72 | 3.66 | 3.71 |
| Autumn | starter Kimchi | 3.89 | 3.78 | 3.71 | 3.7 |

As shown from the table 4, general taste preference for the naturally fermented Kimchi shows a wide deviation depending on manufacture season, i.e., a value of 3.59 for the summer Kimchi to a value of 4.01 for the winter Kimchi. On the other hand, the Kimchi manufactured with a starter *Leuconostoc citreum* CJGN34 shows a narrower deviation of the taste quality, i.e., a value of 3.85 for the summer Kimchi to a value of 4.05 for the winter Kimchi, which means that *Leuconostoc citreum* CJGN34 has a significant effect in providing Kimchi with a constant fermentation quality throughout a year. Especially, the naturally-fermented summer Kimchi shows lower values for sourness preference, carbonated taste preference and aftertaste preference with a lower value of about 3.5 for general taste preference. However, the starter Kimchi has a variation of sourness preference and aftertaste preference within 95% significance, a variation of carbonated taste preference within 90% significance and a variation of general taste preference within 95% significance, which means that deterioration of fermentation quality of the summer Kimchi was effectively inhibited.

The molar ratio of lactic acid to acetic acid which is a main remark showing fermentation type among hetero fermentation and homo fermentation shows that the starter summer Kimchi has a lower value compared to the naturally-fermented summer Kimchi. Such result indicates that the starter *Leuconostoc citreum* CJGN34 normally dominated, inhibited homo fermentation- or hetero fermentation-lactic acid bacteria and effectively controled deterioration of Kimchi fermentation quality.

The result analyzing organic acids of the Kimchi manufactured in each season is shown in a following table 5.

TABLE 5

| manufacture season | sample | concentration ratio of lactic acid/acetic acid (mM) |
|---|---|---|
| summer | naturally fermentation Kimchi | 2.4 ± 0.3 |
| summer | starter Kimchi | 1.5 ± 0.1 |
| winter | naturally fermentation Kimchi | 1.4 ± 0.2 |
| winter | starter Kimchi | 1.3 ± 0.3 |
| spring | naturally fermentation Kimchi | 1.5 ± 0.1 |
| spring | starter Kimchi | 1.5 ± 0.1 |
| autumn | naturally fermentation Kimchi | 1.4 ± 0.1 |
| autumn | starter Kimchi | 1.4 ± 0.1 |

EXAMPLE 5

Fermented Foods and Pickles Manufactured Using *Leuconostoc citreum* CJGN34 Bacteria as a Starter For applying *Leuconostoc citreum* CJGN34 bacteria according to the present invention to fermentation foods besides Kimchi as a starter, a bacteria culture or a bacteria composition was prepared in the same manner with the Example 4 and used as a starter in manufacturing fermented foods. Fermented foods were made of various raw materials such as cucumber, radish, carrot, onion, garlic, pepper and Korean cabbage. Further, fermented picked radishes were manufactured by applying the starter to picked radishes.

EXAMPLE 6

Preparation and Usage of a Bacteria Composition Containing *Leuconostoc citreum* CJGN34

*Leuconostoc citreum* CJGN34 identified in the Example 1 was mass produced and a bacteria composition was prepared according to the Example 4 as materials of medications, foods, feeds, feed additives or cosmetics.

The prepared bacteria composition was used as feed probiotics after being mixed with feed materials such as grain powder; as medications or food probiotics in a form of tablets or capsules after being mixed with carriers or additives; or as cosmetic materials after being mixed with the other cosmetic materials. The bacteria composition could be utilized in various industries according to conventional methods in the art.

The invention claimed is:

1. A method for preparing fermented foods, comprising:
    preparing a *Leuconostoc citreum* CJGN34 KCTC 10974BP starter preparation from a composition comprising *Leuconostoc citreum* CJGN34 KCTC 10974BP;
    adding the starter preparation to a vegetable to form a vegetable preparation, wherein an amount of the *Leuconostoc citreum* CJGN34 KCTC 10974BP is at least 0.001% based on a weight of the vegetable; and
    fermenting and aging the vegetable preparation.

2. The method of claim 1, wherein the vegetable comprises at least one selected from the group consisting of cucumber, radish, carrot, onion, garlic, pepper and Korean cabbage, and mixtures thereof.

3. The method of claim 1, wherein the fermenting and aging occurs at least in the summer.

4. The method of claim 1, wherein an amount of the *Leuconostoc citreum* CJGN34 KCTC 10974BP is 0.001% to 3% based on a weight of the vegetable.

5. A method for preparing Kimchi, comprising:
    salting a vegetable;
    adding *Leuconostoc citreum* CJGN34 KCTC 10974BP to the salted vegetable to form a Kimchi preparation, wherein an amount of the *Leuconostoc citreum* CJGN34 KCTC 10974BP is at least 0.001% based on a weight of the Kimchi; and
    fermenting and aging the Kimchi preparation.

6. The method of claim 5, wherein the vegetable comprises at least one selected from the group consisting of cucumber, radish, carrot, onion, garlic, pepper and Korean cabbage, and mixtures thereof.

7. The method of claim 5, wherein the fermenting and aging occurs at least in the summer.

8. The method of claim 5, wherein an amount of the *Leuconostoc citreum* CJGN34 KCTC 10974BP is 0.001% to 3% based on a weight of the Kimchi.

9. The method of claim 1, wherein the starter preparation is prepared from a composition comprising powdered *Leuconostoc citreum* CJGN34 KCTC 10974BP.

10. The method of claim 2, wherein the starter preparation is prepared from a composition comprising powdered *Leuconostoc citreum* CJGN34 KCTC 10974BP.

11. The method of claim 3, wherein the starter preparation is prepared from a composition comprising powdered *Leuconostoc citreum* CJGN34 KCTC 10974BP.

12. The method of claim 4, wherein the starter preparation is prepared from a composition comprising powdered *Leuconostoc citreum* CJGN34 KCTC 10974BP.

* * * * *